Figure 1:
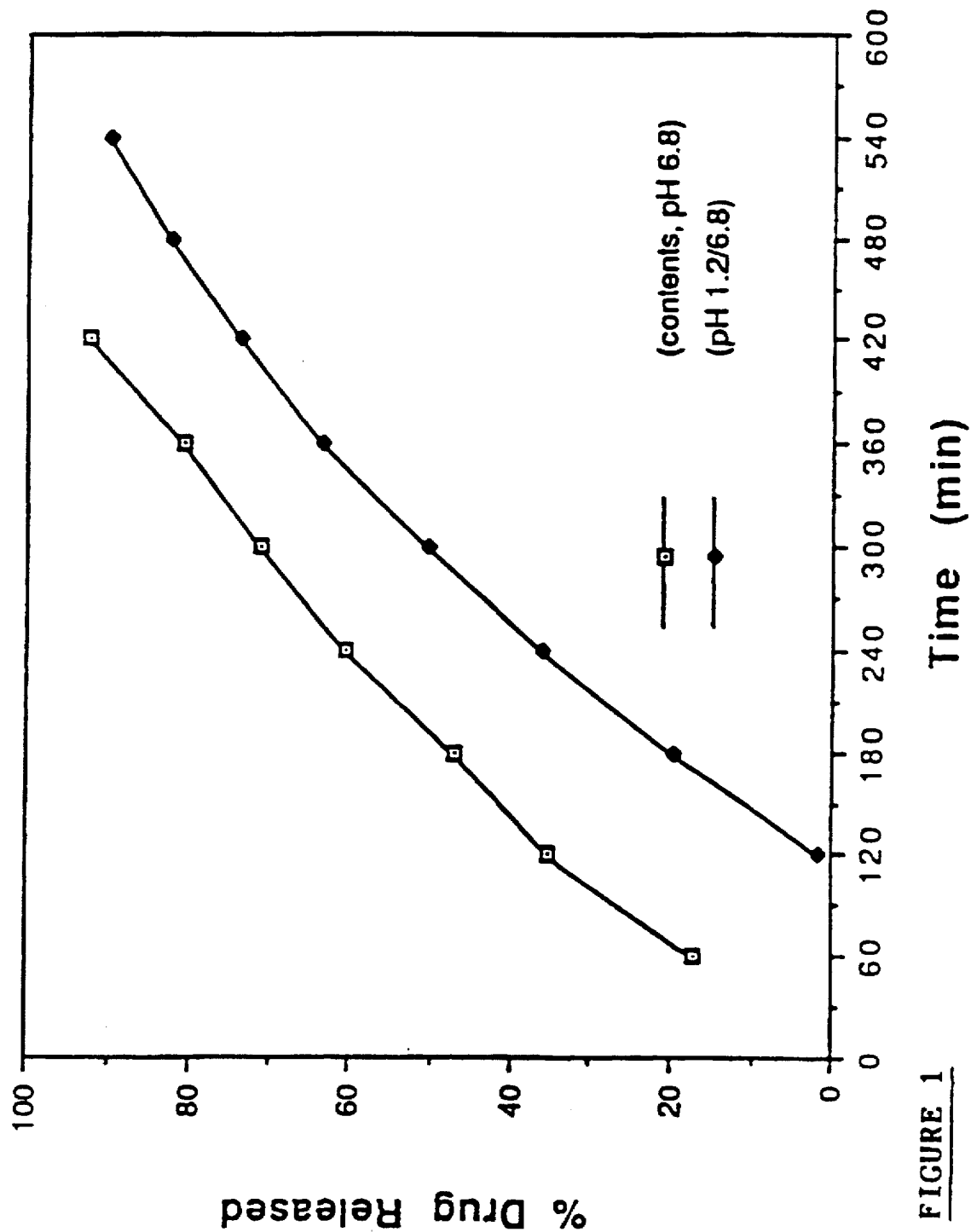

United States Patent [19]

Morella et al.

[11] Patent Number: 5,800,836

[45] Date of Patent: Sep. 1, 1998

[54] PELLETIZED PHARMACEUTICAL COMPOSITION

[75] Inventors: Angelo Mario Morella, Campbelltown; Grant Wayne Heinicke, Fairview Park, both of Australia

[73] Assignee: F. H. Faulding & Co. Limited, Parkside, Australia

[21] Appl. No.: 398,744

[22] Filed: Feb. 6, 1995

Related U.S. Application Data

[63] Continuation-in-part of PCT/AU93/00371 Jul. 23, 1993.

[30] Foreign Application Priority Data

Aug. 5, 1992 [AU] Australia ................. PL3921

[51] Int. Cl.$^6$ ........................................ A61K 9/14
[52] U.S. Cl. ................ 424/489; 424/495; 424/494; 424/497; 424/480
[58] Field of Search ................. 424/489, 495, 424/497, 494

[56] References Cited

U.S. PATENT DOCUMENTS

| | | | |
|---|---|---|---|
| 3,957,523 | 5/1976 | Ohno et al. | 106/189 |
| 4,083,949 | 4/1978 | Benedikt | 424/459 |
| 4,367,217 | 1/1983 | Gruber et al. | 424/494 |
| 4,968,505 | 11/1990 | Okada et al. | 424/400 |
| 5,084,287 | 1/1992 | Ghebre-Sellassie et al. | 424/495 |

FOREIGN PATENT DOCUMENTS

| | | |
|---|---|---|
| 477515 | 1/1973 | Australia . |
| 66156 | 1/1981 | Australia . |
| 0 032562 | 12/1980 | European Pat. Off. . |
| 0 777956 | 10/1982 | European Pat. Off. . |
| 0 148811 | 1/1985 | European Pat. Off. . |
| 0 239361 | 3/1987 | European Pat. Off. . |
| 0 287536 | 3/1988 | European Pat. Off. . |
| 0 391518 | 2/1990 | European Pat. Off. . |
| 519870 | 6/1992 | European Pat. Off. . |
| 93 91 5549 | 4/1995 | European Pat. Off. . |
| 2232048 | 4/1974 | France . |
| 2237620 | 7/1974 | France . |
| 59 010 512 | 7/1982 | Japan . |
| 62-135419 | 6/1987 | Japan . |
| 2132887 | 11/1983 | United Kingdom . |
| 2221842 | 5/1989 | United Kingdom . |
| 86/00306 | 9/1986 | WIPO . |
| 91/00688 | 4/1991 | WIPO . |

*Primary Examiner*—Thurman K. Page
*Assistant Examiner*—William E. Benston, Jr.
*Attorney, Agent, or Firm*—Darby & Darby

[57] ABSTRACT

A pelletized sustained release pharmaceutical composition including a core element including approximately 0.1 to 95% by weight, based on the total weight of the core element, of an active ingredient of low aqueous solubility; approximately 0.1 to 55% by weight of a core seed; and a core coating for the core element, including approximately 30 to 97% by weight, based on the total weight of the core coating, excluding filler, of an enteric polymer; approximately 3 to 50% by weight of an insoluble polymer; and 0 to approximately 50% by weight of plasticizer, the enteric polymer comprising at least approximately 70% by weight of the total weight of the enteric polymer and insoluble polymer; the core coating being such that the active ingredient is released in a controlled fashion over an extended period in the intestine but substantially no release occurs in the acid environment of the stomach and blood levels of active ingredient are maintained within the therapeutic range over an extended period of time.

14 Claims, 1 Drawing Sheet

PELLETIZED PHARMACEUTICAL COMPOSITION

This is a continuation-in-part of International Application No. PCT/AU93/00371 filed Jul. 23, 1993.

The present invention relates to a sustained release pharmaceutical composition, in particular a sustained release pharmaceutical composition including an active ingredient of low aqueous solubility, and to a method of preparing same. The invention is particularly suitable for active ingredients comprising a non steroidal anti-inflammatory ingredient, but the invention is not limited thereto.

As is known in the prior art, it is desirable in the treatment of a number of diseases, both therapeutically and prophylactically to provide the active pharmaceutical ingredient in a sustained release form. Desirably the sustained release provides a generally constant rate of release over an extended period. Whilst there is known in the prior art numerous sustained release formulations, the extension of sustained release regimens to active ingredients of low solubility, in particular non-steroidal anti-inflammatory agents (NSAID's), has been limited. NSAID's are widely used pharmaceuticals, for example in the treatment of acute and chronic pain, particularly pain associated with degenerative diseases such as arthritis. It has been found in the prior art that in particular NSAID's of very slight solubility in water tend to generate a product which is susceptible to low bioavailability. Also it has been found that release of the active ingredient from formulations disclosed in the prior art may be delayed for a time but once release begins, the rate of release is very high and similar to the phenomenon known as "Dose Dumping", which in turn may lead to rapid increase in plasma concentration, to high levels thereby producing undesirable side effects. Such fluctuations in the plasma concentrations of active ingredient may also increase the likelihood of toxicity.

Whilst controlled dosage forms are known in the prior art, in general these formulations use enteric coatings which have the disadvantage that once the formulation passes the gastric environment the coating thereon begins to dissolve rapidly and completely resulting in dose dumping phenomenon. Formulations which use a sustained release coating have also been proposed in the prior art. However these have the disadvantage that partial dissolution often occurs in the gastric environment which may produce irritation in the gut from active ingredient such as an NSAID coming into contact with the gastric mucosa. Other certain active ingredients are degraded in the stomach environment and therefore exposure to the low pH gastric environment is desirably avoided. A further disadvantage of the known formulations is that they require relatively thick coats compared to those disclosed in this invention, which increases manufacturing costs, and manufacturing difficulties. Many of the formulations disclosed in the prior art require blends of coated and uncoated pellets to achieve this sustained release. With this invention, blends of previously coated pellets are not generally required although they may be used successfully while using the art of this invention.

Accordingly, it is an object of the present invention to overcome, or at least alleviate, one or more of the difficulties related to the prior art.

Accordingly, in a first aspect of the present invention there is provided a pelletised sustained release pharmaceutical composition including a core element including at least one active ingredient of low aqueous solubility; and a core coating for the core element, including
at least one enteric polymer which is substantially insoluble at acidic pH but at least partially soluble at less acidic to basic pH; and
at least one polymer which is insoluble independent of pH within the gastrointestinal tract;

the core coating being such that the active ingredient is released in a controlled fashion over an extended period in the intestine but substantially no release occurs in the acid environment of the stomach and blood levels of active ingredient are maintained within the therapeutic range over an extended period of time.

By "acidic pH" as used herein we mean pH in the range 0.5 to 4.5 and more preferably in the range 1.0 to 2.0. By "less acidic to basic pH" as used herein we mean pH in the range 5.0 to 9.0 and more preferably in the range 6.0 to 7.5.

By "sustained release" as used herein we mean release of active ingredient at such a rate that the dosing frequency required to achieve equivalent or better time periods within 24 hours where the plasma level of the drug is within the therapeutic range is decreased.

By "bioavailability" as used herein we mean the extent to which the active drug ingredient is absorbed from the drug product as measured by the area under the plasma concentration vs time curve (AUC).

By "active ingredients of low aqueous solubility" as used herein we mean active ingredients having an aqueous solubility of approximately 1 in 1,000 to 10,000 (volume in mL).

Suitable active ingredients of low aqueous solubility include for example a xanthine oxidase inhibitor, antiarrhythmic, anticoagulant, gold compound, dopamine agonist, diuretic, anticancer, skelatal muscle relaxant, antimalarial, hormone, antipsychotic, antihistamine, immunosuppressive, antileprosy, carbonic anhydrase inhibitor, antibiotic, antifungal, corticosteroid, MAO-1, vasodilator, thyroid agent, sympatholytic, $H_2$-antagonist, stimulant, anticoagulant, anticonvulsant, antituberculosis, hypoglycaemic, glucocorticoid or antidepressant agent.

The active ingredient of low aqueous solubility may be an NSAID or an acid or salt thereof. The NSAID ingredient in the pelletised sustained release pharmaceutical composition according to the present invention may be selected from low aqueous solubility forms of Diclofenac, Etodolac, Fenoprofen, Fluorbiprofen, Ibuprofen, Ibuproxan, Indomethacin, Ketoprofen, Ketorolac, Nabumetone, Naproxen, Phenylbutazone, Piroxicam, Priprofen, Tolmetin, Aspirin, Sulindac, Diflunisal, Indoprofen, Mefanamic Acid, Fenclozic Acid, Alclofenac, Bucloxic Acid, Meclofenamic Acid, Flufenamic Acid, Cinchophen Cinmetacin, Ibufenac, Furobufen, Prodolic Acid, Oxoproxin, Clonixin, Fluprofen, Flutiazin. The present invention is particularly applicable to NSAID's of low aqueous solubility. Diclofenac, Ketorolac and Indomethacin are preferred.

The active ingredient of low aqueous solubility may be any other suitable ingredient, for example low aqueous solubility forms of Allopurinal, Amiodarone Hydrochloride, Anisindione, Auranofin, Benzocaine, Bromocriptine Mesylate, Bumetanide, Busulfan, Chlorambucil, Chloroquine, Chlorphenesin Carbomate, Chloprothixene, Clemastine Fumarate, Dehydrocholic Acid, Dichlorphenamide, Doxycycline Monohydrate, Erythromycin, Etoposide, Griseofulvin, Haloperidol, Hydrocortisone, Levothyroxine Sodium, Liothyronine Sodium, Lovastafin, Mephenytoin, Methazolamide, Methclothiazide, Metyrosine, Nitrofarantoin, Norfloxacin, Oestropipate, Famotadine, Pemoline, Phenacemide, Pimozide, Quinethazone, Rifampin, Sulfisoxazole, Tamoxifen Citrate, Tetracycline, Tolazamide, Triamcinolone, Trichlormethiaside, Trimethoprim, Trimipramine Maleate, Uracil Mustard and acids or salts thereof.

It has been found that when the active ingredient was the acid form of Diclofenac, which is less soluble than the more common Diclofenac sodium, this resulted in a product with better bioavailability than a product made with the more soluble Diclofenac sodium when both products had equivalent in vitro release at pH 6.8. The composition of the present invention resulted in a higher bioavailability for the less soluble form than equivalent in vitro release of the more soluble form. This is the opposite result to that which would have been expected according to current teachings and the prior art. Following the current teachings, the less soluble form should have resulted in a lower bioavailability than the more soluble form. This fact illustrates the surprising finding that the compositions of the present invention are especially suitable for active ingredients of low aqueous solubility.

Accordingly in a preferred aspect of the present invention, there is provided a pelletized sustained release pharmaceutical composition including a core element including approximately 0.1 to 95% weight, based on the total weight of the core element of an active ingredient of low aqueous solubility, approximately 0.1 to 55% by weight weight binding agent;

approximately 5 to 99% weight of a core seed; and a core coating for the core element, including approximately 30 to 97% by weight, based on the total weight of the core coating, excluding filler, of an enteric polymer;

approximately 3 to 50% by weight of an insoluble polymer; and 0 to approximately 50% by weight of plasticizer, the enteric polymer comprising at least approximately 70% by weight of the total weight of the enteric polymer and insoluble polymer;

the core coating being such that the active ingredient is released in a controlled fashion over an extended period in the intestine but substantially no release occurs in the acid environment of the stomach and blood levels of active ingredient are maintained within the therapeutic range over an extended period of time.

The pelletised composition of the present invention may comprise a relatively thin coated pellet which slowly releases an active ingredient of low solubility over an extended period of time, once the pellet has passed the gastric environment. The composition exhibits controlled released properties in vivo and avoids high plasma concentrations. The composition when in the form of controlled release pellets alleviates the need to manufacture and blend immediate and sustained release forms to achieve suitable bioavailability and pharmacokinetic parameters as disclosed in the prior art. The pelletised composition allows for changes in release characteristics to be undertaken with ease, by altering potency, coat weight, seed size, and/or the precise polymer blend used in the coat. The composition also provides a decreased dosing frequency, thereby improving patient compliance. The dosage form of the composition is also of an acceptable size, aesthetic appeal, and palatable nature to the patient.

The active ingredient of low aqueous solubility may be present in the core in any suitable effective amount. The active ingredient of low aqueous solubility is present in amounts of approximately 0.1 to 95% by weight, preferably approximately 2.5 to 55% by weight, based on the total weight of the core element. If the active ingredient has pH dependent solubility characteristics or if otherwise desired,
an acid may be included in the core to maintain a desirable pH. The acids may be organic or inorganic acids. Organic acids include: Asorbic, Citric, Adipic, Fumaric, Tartaric, Succinic, Malic, Alginic, Benzoic, Sorbic. Inorganic acids include: hydrochloric, ammonium chloride, ammonium phosphate (mono and di basic), ammonium sulphate, ammonium bisulphate, potassium or sodium phosphate (mono and di basic) and the like.

The binding agent is present in amounts of from approximately 0.1 to 55% preferably 0.1 to 20% by weight based on the total weight of the core element. The binding agent may be of any suitable type. Suitable binders may be selected from polyvinylpyrrolidone (povidone), hydroxypropyl cellulose, hydroxypropyl methylcellulose, methylcellulose, hydroxyethyl cellulose, sugars and mixtures thereof. The binding agent may be provided in the form of a granulating solution. An aqueous or organic solvent may be included. Methanol, ethanol or mixtures thereof may be used as solvents.

The core seed may be of any suitable type. A sugar sphere may be used. The size and amount of the core seed may vary substantially depending upon the amount of active ingredient to be included. Accordingly, the core seeds may vary from approximately 5.0 to 99% by weight, preferably 40 to 90% by weight based on the total weight of the core element. The core seed may be of such a diameter to provide a final core element having a diameter of approximately 500 to 2000 um.

Suitable core fillers may be selected from insoluble materials such as silicon dioxide, talc, titanium dioxide, alumina, starch, kaolin, polacrilin potassium, powdered cellulose, microcrystalline cellulose and the like or mixtures thereof. Soluble fillers may be selected from mannitol, urea, sucrose, lactose, dextrose, sodium chloride, sorbitol and mixtures thereof.

In a further preferred aspect, the core element according to this aspect of the present invention may further include other carriers or excipients, stabilizing agents, glidants, dissolution accelerants such as potassium dihydrogen phosphate, and colourants.

The core filler may be present in amounts of from 0 to approximately 75% by weight, preferably 5.0 to 60% by weight, based on the total weight of the core element.

The amounts of the various constituents which comprise the core (based on total weight of core):

| Active Ingredient | 0.1–95 | Preferably | 2.5–55 |
|---|---|---|---|
| Binder | 0.1–45 | Preferably | 0.1–20 |
| Core Seed | 5–99 | Preferably | 40–90 |

The size of the core seed may vary from about 0.1–1.7 mm depending upon the amount of active to be included and the desired final size of the core element.

The amounts of the various constituents of the core may be as follows:

| Active Ingredient | 10–70% |
|---|---|
| core seed | 25–80% |
| filler | 5.0–60% |
| binder | 0.1–55% |
| solvent* | 70–99% |

*not present in final formulation.

The pharmaceutical composition according to this aspect of the present invention further includes a core coating. It will be understood that the core coating will substantially eliminate dissolution in the acidic environment of the stomach but will dissolve sufficiently to permit release in a controlled fashion over an extended period in the environment of the intestines.

The core coating includes approximately 30 to 97% by weight, based on the total weight of the core coating, excluding filler, of an enteric polymer; and approximately 3 to 50% by weight of an insoluble polymer.

The enteric polymer, whilst substantially insoluble at acidic pH may dissolve in the less acidic to basic pH encountered in the small intestine.

The insoluble polymer component is insoluble independent of pH.

The enteric polymer component may be any one or more of the following polymers: cellulose butyrate phthalate, cellulose hydrogen phthalate, cellulose propionate phthalate, polyvinyl acetate phthalate, cellulose acetate phthalate, cellulose acetate trimellitate, hydroxypropyl methylcellulose phthalate, hydroxypropyl methylcellulose acetates, dioxypropyl methyl cellulose succinates, acrylic methacrylic acid copolymers (Eudragits®), shellac, Sandarac®, copal collophorium, cellulose acetate phthalate and mixtures thereof.

Preferably the enteric polymers may dissolve at a pH of 5.0–9.0 and more preferably a pH of about 6.0–7.5.

The insoluble polymer may be any one or more of the following polymers: ethyl cellulose, cellulose acetates and their esters, acrylic methacrylic acid copolymers (Eudragit NE30D), hydroxypropyl methyl cellulose acetate and mixtures thereof. Preferably the insoluble polymer is ethyl cellulose.

A core coating including at least approximately 70% by weight of enteric polymer, based on the weight of enteric polymer and insoluble polymer, is particularly preferred.

The core coating may further include at least one plasticizer; and optionally at least one filler.

The at least one plasticiser may be selected from diethyl phthalate, triethyl citrate, triethyl acetyl citrate, triacetin, tributyl citrate, polyethylene glycol, glycerol and mixtures thereof. It will be understood that the plasticiser used may be largely dictated by the polymer used in the coating formulation.

The plasticiser may be present in amounts of from 0 to 50% by weight preferably 2.5 to 30% by weight based on the total weight of the core coating before the addition of filler have been found to be suitable.

The filler may be selected from those insoluble fillers listed above for the manufacture of the core element.

The filler may be present in amounts of from 0 to approximately 75% by weight, preferably 5 to 60% by weight, based on the total weight of the core coating have been found to be suitable.

The core coating may include a water soluble component. It is preferred that a water soluble component be present in an amount such that substantially no release occurs in the stomach but such that the cores are wetted to reduce lag times for dissolution in the intestine. In general, the more insoluble the active ingredient, the greater the amount of water soluble component that may be present.

A core coating composition may be provided in the form of a solution, dispersion or suspension.

The solvent or dispersion medium may be present in amounts of from approximately 25 to 97% by weight based on the total weight of the core coating composition. The solvent for the polymer blend may be an aqueous or organic solvent. The solvent/dispersion medium for the polymer blend may be selected from water, methanol, ethanol and methylene chloride and the like or mixtures thereof.

The amounts of the various constituents of the core coating (given in % weights based on the total weight of the core coating excluding weight of filler and plasticizer) may be as follows:

|  | Approx. | Preferably | More Pref. |
|---|---|---|---|
| Insoluble Polymer Component | 3–50 | 5–40 | 10–35 |
| * Fillers | 0–75 | 0–60 | 0–40 |
| Enteric Component | 30–97 | 40–90 | 50–85 |
| Water Soluble Component | 0–66 | 0–40 | 0–25 |
| * Plasticizer | 0–50 | 2.5–30 |  |

* = Based on total weight of coat.

The specific ratios of components will depend on the solubility of the active ingredient.

In a further aspect of the present invention, there is provided a method for preparing a pelletised sustained release pharmaceutical composition, which method includes providing a core element including approximately 0.1 to 95% weight, based on the total weight of the core element of an active ingredient of low aqueous solubility, approximately 0.1 to 55% by weight of a binding agent;

approximately 5 to 99% weight of a core seed; and a core coating for the core element, including approximately 30 to 97% by weight, based on the total weight of the core coating, excluding filler, of an enteric polymer;

approximately 3 to 50% by weight of an insoluble polymer, the enteric polymer comprising at least approximately 70% by weight of the total weight of the enteric polymer and insoluble polymer;

introducing the core element into a fluidisied bed; and spraying the core coating composition onto the core element.

In a preferred aspect the method may further include the preliminary steps of providing an active ingredient of low aqueous solubility;

a binding agent; and a core seed; and coating the core seeds with the active ingredient and binding agent to form a core element.

In a preferred form the binding agent may be provided in a granulating solution. In this form the coating step may be conducted as a spheronisation process. The spheronisation process includes contacting the core seeds with the active ingredient and simultaneously adding the granulating solution thereto. The spheronisation process may be conducted in a spheronising machine.

In a further alternative aspect of the present invention, the method may further include the preliminary steps of providing an active ingredient of low aqueous solubility;

a binding agent; and an effective amount of a solvent or granulating liquid;

mixing the ingredients; and subjecting the ingredients to an extrusion followed by marumerisation to form a core element.

The solvent may be an aqueous or organic solvent or mixtures thereof. The solvent may be present in an amount effective to allow the ingredients to be extruded.

The core elements formed are then subjected to a drying step. The drying step may be conducted in a fluidised bed or drying oven.

In an alternative form the binding agent and active ingredient are provided in a solution or slurry. In this form the core seeds are sprayed with the solution or slurry. The spraying step may be conducted in any suitable coating equipment. The coating equipment may be a fluidised bed, preferably a rotary fluid bed machine.

Spray coating of core elements may be undertaken utilising bottom, top or tangentially located spray nozzles. A bottom spray nozzle may reside proximate to the base of the fluidised bed facing upwards while a top spraying nozzle is located above the contents of the bed facing downwards. The spray nozzle may reside in the mid-section of the fluidised bed and be oriented such as to spray tangentially to the rotating core elements.

A spray-dried seed core element or an extruded/marumerized core element are preferred.

The finished product may be from about 0.5 to 2.0 mm, more preferably from about 0.7 to 1.4 mm, in size.

The finished product may be in multi-pellet, hard gelatin capsule, sprinkle sachet, or tabletted form.

The method of treatment according to this aspect of the present invention is particularly applicable to the treatment of acute and chronic conditions, such as pain associated with degenerative diseases such as arthritis and the like.

Accordingly, in a further aspect of the present invention there is provided a method for the therapeutic or prophylactic treatment of conditions in patients requiring such treatment which method includes administering to a patient an effective amount of a pelletised sustained release pharmaceutical composition, as described above, including an active ingredient of low solubility, selected from diclofenac, ketoroloc and indomethacin.

Preferably the pharmaceutical sustained release composition is provided in a unit dosage form and administration occurs at intervals of approximately 8 to 24 hours.

The pelletised sustained release pharmaceutical composition may be administered with a longer dosage interval to that used in the prior art. The multi-pellet encapsulated form may for example be administered every eight to twenty-four hours in sustained release form depending on the nature of the active ingredient.

It will be understood that since the active ingredient is provided in a sustained release pellet form with uniform release characteristics significantly less fluctuations in plasma concentrations of active ingredients over a 24 hour period are encountered, and this occurs with less frequent dosing relative to the active ingredient in an uncoated form or in forms with mixtures of uncoated and enteric coated forms. This is expected to result in less toxicity problems and more effective therapeutic activity.

Moreover, the pharmaceutical pellet composition according to the present invention shows no evidence of dose dumping phenomena. The relative bioavailability of the active ingredient generated from the pharmaceutical pellet composition is not compromised by food even with drugs which are known to have problems with bioavailability when administered with food, such as erythromycin. Compliance will improve because the product may be taken without regard to meals.

The present invention will now be more fully described with reference to the accompanying examples. It should be understood, however, that the following description is illustrative only and should not be taken in any way as a restriction on the generality of the invention specified above.

1. Formulation 1

Core Composition

| | |
    |---|---|
    | Diclofenac | 277.0 g |
    | Sugar spheres | 500.0 g |
    | Colloidal silicon dioxide | 2.8 g |
    | Polyvinyl pyrrolidone | 29.0 g |
    | Water* | 151.0 g |

Core Coating Composition 1

| | |
    |---|---|
    | Ethylcellulose | 16.3 g |
    | Hydroxypropyl methylcellulose phthalate | 42.4 g |
    | Diethyl phthalate | 6.6 g |
    | Talc | 19.6 g |
    | Ethanol* | 831.0 g |
    | Water* | 147.0 g |

2. Formulation 2

Core Composition 2

| | |
    |---|---|
    | Diclofenac | 280.0 g |
    | Core seeds | 500.0 g |
    | Hydroxypropyl cellulose | 5.0 g |
    | Colloidal silicon dioxide | 2.8 g |
    | Water* | 90.0 g |

Core Coating Composition 2

| | |
    |---|---|
    | Ethylcellulose | 18.4 g |
    | Hydroxypropyl methylcellulose phthalate | 64.4 g |
    | Diethyl phthalate | 9.2 g |
    | Talc | 27.6 g |
    | Ethanol* | 1174.0 g |
    | Water* | 207.0 g |

3. Formulation 3

Core Composition 3

| | |
    |---|---|
    | Indomethacin (acid) | 3.117 kg |
    | Sugar spheres | 5.88 kg |
    | Polyvinyl pyrrolidone | 0.6 kg |
    | Kaolin | 0.311 kg |
    | Water* | 1.2 kg |

Core Coating Composition 3

| | |
    |---|---|
    | Ethylcellulose | 0.331 kg |
    | Hydroxypropyl methylcellulose phthalate | 1.721 kg |
    | Diethyl phthalate | 0.148 kg |
    | Methanol* | 17 kg |
    | Methylene chloride* | 17 kg |

4. Formulation 4

Core Composition 4

| | |
    |---|---|
    | Erythromycin (free base) | 660.0 g |
    | Polyvinylpyrrolidone | 34.0 g |
    | Potassium dihydrogen phosphate | 36.0 g |
    | Hydroxypropyl cellulose | 15.5 g |
    | Microcrystalline cellulose | 56.0 g |
    | Water* | 200.0 g |

Coating Composition 4

| | |
    |---|---|
    | Hydroxypropyl methylcellulose phthalate | 63.0 |
    | Ethylcellulose | 17.0 |
    | Diethylphthalate | 20.0 |
    | Methanol* | 1500.0 |
    | Methylene chloride* | 1500.0 |
    | Talc | 56.0 g |

5. Formulation 5

Core Composition 5

| | |
    |---|---|
    | Ketorolac | 286 g |
    | Sugar Spheres | 699 g |
    | Hydroxypropyl cellulose | 15 g |
    | Water | 300 g |

Core Coating Composition 5

| | |
    |---|---|
    | Ethyl cellulose | 23.8 g |
    | Hydroxypropyl methylcellulose phthalate | 134.2 g |

-continued

| | | |
|---|---|---|
| | Diethyl phthalate | 17.6 g |
| | Ethanol | 2816 g |
| | Water | 704 g |
| 6. | Formulation 6 | |
| | Core Composition 6 | |
| | Ketorolac trimethamine | 286 g |
| | Fumaric acid | 286 g |
| | Sugar Spheres | 400 g |
| | Hydroxypropyl cellulose | 28.6 g |
| | Water | 300 g |
| | Core Coating Composition 6 | |
| | Ethylcellulose | 23.6 g |
| | Hydroxypropyl methylcellulose phthalate | 134.2 g |
| | Diethyl Phthalate | 17.6 g |
| | Ethanol | 2816 g |
| | Water | 704 g |
| 7. | Formulation 7 | |
| | 51.6 g of pellets were used for the trial. These pellets contained: | |
| | Diclofenac | 14.21 g |
| | Hydroxypropyl cellulose | 0.85 g |
| | Core seeds | 30.5 g |
| | Core Coating Composition 7 | |
| | Talc | 1.4 g |
| | Ethylcellulose | 0.82 g |
| | Hydroxypropyl methylcellulose phthalate | 3.37 g |
| | Diethyl phthalate | 0.47 g |

Spheronised Core Manufacture (Core Composition 1 2, 3, 5, 6 and 7)

The sugar spheres were placed in a spheroniser. The sugar spheres were then coated with a dry mixture of the active ingredients and inactive excipients whilst concomitantly adding a solution of the binder components.

The wet cores so formed were then dried in a fluidised bed for 1 hour.

Core Manufacture (Core Composition 4)

The ingredients were wet massed and subjected to a extrusion/marumersation process.

Pellet Manufacture (a) The dried spheronised cores 1, 2, 3, 5, 6 and 7 were then placed in a fluid bed coating apparatus. The core coating compositions 1, 2, 3, 5, 6 and 7 were then sprayed onto the cores 1, 2, 3, 5, 6 and 7 to form Formulation 1, 2, 3, 5, 6 and 7 pellets respectively. At the conclusion of the process, the pellets were fluid bed dried.

(b) The core coating composition 4 was applied to 750 g of dried extruded cores in a fluidised bed.

A dissolution test was conducted on the pellet compositions 1, 2, 3, 4 and 7 utilising the test method USPXXII 1990 (Test 711). The sample is placed in an aqueous medium previously degassed and equilibrated to 37° C. The media are USP pH 1.2 media without enzymes and pH 6.8 phosphate buffer. A sample of known volume is withdrawn at designated time intervals from the bath as directed and subjected to a suitable assay procedure. The mg of active as a function of time is plotted as the dissolution profile. The dissolution profile of formulation 7 is shown as FIG. 1.

The tests were conducted at pH 1.2 followed by 6.8.

TABLE 1

Dissolution Data for Formulation 1 at pH 6.8 after exposure to acid pH 1.2 for 2 hours (n = 3)

| Time | Mg Rel | SD | % Rel | SD |
|---|---|---|---|---|
| 30 | 11.78 | 0.07 | 9.6 | 0.06 |
| 60 | 20.8 | 0.07 | 17.0 | 0.07 |
| 120 | 37.8 | 0.00 | 31.0 | 0.02 |
| 180 | 53.0 | 0.13 | 43.4 | 0.08 |
| 240 | 66.7 | 0.07 | 54.6 | 0.07 |
| 300 | 77.2 | 1.05 | 63.3 | 0.86 |
| 360 | 86.8 | 0.45 | 71.0 | 0.36 |

% released in acid 0.02 ± 0.00

TABLE 2

Dissolution Data for Formulation 2 at pH 6.8 after exposure to acid pH 1.2 for 2 hours (n = 3)

| Time | Mg Rel | SD | % Rel | SD |
|---|---|---|---|---|
| 30 | 9.0 | 0.00 | 8.8 | 0.06 |
| 60 | 16.9 | 0.16 | 16.5 | 0.27 |
| 120 | 31.0 | 0.21 | 30.2 | 0.21 |
| 180 | 43.8 | 0.21 | 42.7 | 0.50 |
| 240 | 55.7 | 0.21 | 54.3 | 0.41 |
| 300 | 67.2 | 0.44 | 65.6 | 0.85 |
| 360 | 77.5 | 0.47 | 75.6 | 0.98 |
| 420 | 87.1 | 0.56 | 85.0 | 1.09 |

% released in acid 0.77 ± 0.15

TABLE 3

Dissolution Data for Formulation 3 at pH 6.8 after exposure to acid pH 1.2 for 2 hours (n = 3)

| Time | Mg Rel | SD | % Rel | SD |
|---|---|---|---|---|
| 60 | 14.3 | 0.94 | 17.4 | 1.3 |
| 120 | 25.1 | 0.96 | 30.6 | 0.9 |
| 240 | 42.7 | 2.16 | 52.1 | 2.0 |
| 360 | 56.7 | 2.48 | 69.1 | 2.1 |
| 480 | 66.4 | 1.98 | 81.0 | 1.4 |

TABLE 4

| Time | % Rel | SD |
|---|---|---|
| Dissolution Data for Formulation 4 at pH 6.8 (n = 3) | | |
| 30 | 13.1 | 0.41 |
| 60 | 29.9 | 1.09 |
| 120 | 56.0 | 1.67 |
| 180 | 75.7 | 2.07 |
| 240 | 87.9 | 1.90 |
| Dissolution Data for Formulation 4 at pH 6.8 after exposure to acid pH 1.2 for 2 hours (n = 3) | | |
| 60 | 28.4 | 0.89 |
| 120 | 54.2 | 1.31 |
| 180 | 73.0 | 1.64 |
| 240 | 86.1 | 0.83 |
| 300 | 95.5 | 1.45 |

SD = Standard deviation

IN-VIVO STUDIES OF FORMULATION 1, 3, 4 AND 7

Two sustained release NSAID compositions and one composition containing an active ingredient of low aqueous solubility which is not a NSAID in accordance with the present invention have been trialled in healthy volunteers (fasting). The results of these trials suggest that the applicant has a product that is superior to commercial products with regard to controlled delivery and sustained release of these compounds from the 3 formulations. An investigation has also been initiated into understanding the effect that food has on the absorption of the drugs from these formulations.

The sustained release oral compositions according to the present invention are designated Formulation 1, Formulation 3, Formulation 4 and Formulation 7.

1. PART A Formulation 1

A single dose 3 way crossover study under fasted conditions was conducted in nine healthy volunteers. On 3 occasions separated by one week, subjects received a 100 mg oral diclofenac dose as either a solution (reference dose) or one of two sustained release formulations as pellets contained within a capsule (designated Formulation 1) and a second test formulation based on the sodium salt with similar dissolution characteristics of diclofenac.

The doses were administered after a 12 hour overnight fast. Venous blood samples were taken at specified time intervals from immediately prior to dose administration and for 24 hours following administration of the sustained release formulations and for 8 hours after the reference solution dose. The diclofenac concentration in the blood samples was quantitated using high pressure liquid chromatography (HPLC). Table 3.1 summarises the mean area under the curve (AUC); $C_{max}$ (maximum observed plasma concentration), $t_{max}$ (time to reach maximum observed plasma concentration); $t_{1/2}$ (apparent terminal half life); $t \geq 0.75 \, t_{max}$ (time for which the plasma concentration was greater than or equal to 75% of $C_{max}$) and relative bioavailability (F %).

The results suggested that Formulation 1 provided a sustained release relative to the reference solution as assessed by:

(1) a lower $C_{max}$ for the formulations;
(2) a longer $t_{max}$ for the formulations; and
(3) a longer time for which the plasma diclofenac concentration was greater than or equal to 75% $C_{max}$ for the formulations.

There was a significant decrease in $C_{max}$ value compared with the reference solution. The mean (±SD) $C_{max}$ value for the solution was 5.8±2.3 ng/mL whereas the corresponding value for Formulation 1 was 0.5±0.2 ng/mL.

The variability in $C_{max}$ for Formulation 1 demonstrated by the coefficient of variation was significantly less than that of the solution in the same subjects.

There was a significant increase in $t_{max}$ values for the formulation relative to that obtained with the reference solution. The mean (±SD) $t_{max}$ values for solution was 0.3±0.1 hours whereas the equivalent value was 3.9±0.8 hours. The variability in $t_{max}$ values for the formulations were less than those obtained for the solution in the same subjects.

The time the plasma diclofenac concentration was greater than or equal to 75% $C_{max}$ was significantly greater for substained release Formulation 1 compared to the reference solution dose. The mean time was 1.6±0.5 hours for Formulation 1 compared to only 0.23±0.1 hours for the reference solution. Expressing these data as percentage of the time of the reference solution, Formulation 1 has 613% greater time when the plasma diclofenac concentration was greater than or equal to 75% $C_{max}$ compared to the solution.

There was a slight reduction in AUC for Formulation 1 than that obtained for the reference solution.

The relative bioavailability for the formulation was calculated from the ratio of the AUC for the appropriate formulation relative to that obtained for the reference solution for each subject. The relative bioavailability was 66% for Formulation 1.

The AUC and relative bioavailability data suggested that the extent of absorption of diclofenac from Formulation 1 and the solution is similar. The $C_{max}$, $t_{max}$ and $t \geq 0.75 \, C_{max}$ data however suggest that Formulation 1 exhibits the typical slower and prolonged absorption of a true sustained release preparation.

TABLE 3.1

RESULT OF STUDY PART A

| PARAMETER | SOLUTION Mean | FORMULATION 1 Mean | OBSERVE DIFF |
|---|---|---|---|
| AUC (ng.h/mL) | 3.051 | 2.017 | −33.9 |
| SD | 0.650 | 0.617 | |
| CV % | 21 | 31 | |
| $C_{max}$ (ng.h/mL) | 5.775 | 0.484 | −91.6 |
| SD | 2.326 | 0.169 | |
| CV % | 40 | 35 | |
| $t_{max}$ (hours) | 0.27 | 3.89 | 1340.7 |
| SD | 0.11 | 0.78 | |
| CV % | 41 | 20 | |
| Relative Bioavailability (F %) | 100.0 | 65.6 | −34.4 |
| SD | N.A. | 12.4 | |
| CV % | N.A. | 19 | |
| $t \geq 0.75 \, C_{max}$ (hours) | 0.23 | 1.64 | +613.0 |
| SD | 0.11 | 0.47 | |
| CV % | 48 | 29 | |

2. PART B—Formulation 3

A randomized, balanced single dose 3 way crossover study under fed and fasting conditions was conducted in 30 healthy volunteers. On 3 occasions separated by one week, subjects received a 75 mg oral indomethacin dose as either Indocin SR (reference dose) taken fasting or one sustained release formulation as pellets contained within a capsule (designated Formulation 3 taken under both fasting and fed conditions). The doses were administered either following an overnight fast or within 5 minutes of eating a standard high fat meal. Venous blood samples were collected at specified time intervals immediately prior to the dose and for 30 hours following administration of the dose. The indomethacin concentration in the plasma samples was quantitated using high pressure liquid chromatography (HPLC). Table 3.2 summarises the mean area under the plasma concentration Vs time curve (AUC); $C_{max}$ (maximum observed plasma concentration); $t_{max}$ (time to reach maximum observed plasma concentration); and relative bioavailability (F %).

The results suggest that, both in the presence and absence of food, Formulation 3 provided a sustained release of the drug relative to the reference dose as assessed by:

(1) $C_{max}$ for the formulations;
(2) $t_{max}$ for the formulations.

There was a significant decrease in $C_{max}$ values for the formulation in both the fed and fasting data compared with the reference formulation. The mean (±SD) $C_{max}$ for the reference product was 2.19±0.82 ng/mL whereas the corresponding values for Formulation 3 under fed and fasting conditions were 1.49±0.56 ng/mL and 1.77±0.66 ng/mL respectively. The variability in $C_{max}$ was similar for all dosing regimens. The $C_{max}$ values for Formulation 3 obtained under fed conditions were similar to the values obtained from the same subjects under fasting conditions (Part A).

There was a significant increase in $t_{max}$ values for the formulation when administered in the fed state relative to that obtained with the dose taken fasting. The mean (±SD) $t_{max}$ values for reference and fed doses taken fasting were 2.98±0.97 and 2.89±0.95 hours whereas the equivalent value for the test formulation was 5.89±1.81 in the fed state. The variability in $t_{max}$ values for all the dosing regimens were not significantly different.

Although there was a significant difference between the mean AUC values for the test formulation under fasting and fed conditions, there was no difference between the mean AUC values of the test and reference formulations taken fasting (table 3.2). The mean AUC values were very similar for the test formulation under fasting and fed conditions with mean values of 9.44±2.02 ng.h/mL and 8.88±1.95 ng.h/mL respectively. The mean AUC for the reference formulation under fasting conditions was 10.20±2.55 ng.h/mL. The intersubject variability in AUC was similar for all formulations as shown by the coefficient of variation.

The primary concern was to establish that "dose dumping" did not occur with either dosing regimen. The data indicate that the bioavailability of indomethacin from formulations in the presence of food is at least equivalent to the bioavailability from the same formulation in the fasted state and that absorption of the indomethacin dose from the formulations is not affected by concomitant intake of food.

The relative bioavailability for the formulations relative to that obtained for the reference dose fasting was 89.3% fed and 94.3% under fasting conditions.

The AUC and relative bioavailability data suggest that the extent of absorption of indomethacin from the formulation is similar but slightly less than the reference dose in the fed state whereas the $C_{max}$ and $t_{max}$ data indicate that the formulation exhibits the typical slower and prolonged absorption of a true sustained release preparation.

TABLE 3.2

RESULT OF STUDY PART B

| PARAMETER | INDOCIN SR Fasting | FORMULATION 3 | | | |
|---|---|---|---|---|---|
| | | Mean Fasting | Observ Diff | Mean Fed | Observ Diff |
| AUC (ng.h/mL) | 10.20 | 9.44 | −7.46 | 8.88 | −12.88 |
| SD | 2.55 | 2.02 | | 1.95 | |
| CV % | 25 | 21 | | 22 | |
| $C_{max}$ (ng.h/mL) | 2.19 | 1.77 | −19.18 | 1.49 | −31.76 |
| SD | 0.82 | 0.66 | | 0.56 | |
| CV % | 37 | 37 | | 38 | |
| $t_{max}$ (hours) | 2.98 | 2.89 | −2.97 | 5.88 | 97.74 |
| SD | 0.97 | 0.95 | | 1.81 | |
| CV % | 33 | 33 | | 31 | |
| Relative Bioavailability (F %) | 100.0 | 94.3 | | 89.3 | |
| SD | N.A. | 15.8 | | 17.4 | |
| CV % | N.A. | 17 | | 19 | |

3. PART C—Formulation 4

Relative bioavailability of formulation 4 was determined under fed and fasting conditions in 6 health subjects using Eryc® as a reference dose. Total urinary output was measured by HPLC after administration of 500 mg of erythromycin either following an overnight fast or following a standard high fat meal. Results are summarised in Table 3.3.

The results in Table 3.3 suggest that absorption of erthryomycin from Formulation 4 was not significantly affected by food. The affect of food on erythromycin absorption has been well documented. The insignificant effect of food on erythromycin absorption demonstrated by the dosage form disclosed in this invention is much smaller than that disclosed in the prior art.

TABLE 3.3

| | Eryc fasting | Formulation 4 fasting | Formulation 4 fed |
|---|---|---|---|
| mg Recovered in Urine 0–32 hr | 12.72 | 8.19 | 7.55 |
| SD | 4.37 | 3.16 | 4.10 |
| CV % | 34 | 39 | 40 |

4. PART D—COMPARISON STUDY OF FORMULATION 1, 7 AND VOLTAROL®

Sample Analysis

Study plasma samples (including repeat samples) were analysed for diclofenac concentrations using a sensitive and specific high performance liquid chromatographic (HPLC) procedure involving UV detection. The assay had a limit of quantitation of 0.025 mg/L and was linear over the range 0.025 mg/L to 1.000 mg/L.

Results

The results obtained by comparing the four treatments are summarised in Tables 4 and 5 and FIG. 1. Tables 4A, B and C show the mean (standard deviation) values, percentage difference of the means of the calculated pharmacokinetic parameters and observations, the 90% confidence intervals for the difference between the means of $AUC_{o-t}$ and $C_{max}$ and the results of the nonparametric Friedman test for $T_{max}$. Table 5 shows the mean (standard deviation) plasma diclofenac concentrations at each nominated sampling time and the 90% confidence intervals for the difference between the means.

Discussion

This study examined three formulations—Formulation 1 and Formulation 7, Voltarol® Retard, manufactured by Ciba Geigy. The bioavailability of the formulations relative to Voltarol® Retard was determined by comparison of area under the plasma concentration versus time curve (AUC) values. These values were determined from time zero to the time of the last measurable concentration. Extrapolation to infinite time was not possible because of the inability to accurately determine the elimination rate constant due to apparent enterohepatic cycling. From the data presented in the report, the following conclusions can be made:

(1) Voltarole Retard, when administered following a high-fat meal did not exhibit satisfactory sustained-release profiles in subjects 3, 4, 6, 9, 10 and 11, but showed evidence of dose-dumping. Neither formulation showed evidence of dose-dumping even when Formulation 7 was administered following the identical high-fat meal. Both formulations showed a slower rate of input which was relatively uniform for each subject. This can be seen from the range of values of the ratio of AUC from time zero to time of maximum plasma concentration and AUC from time zero to time of the last measured concentration. For Formulation 7 with food, the range was 0.214 to 0.578 (i.e. 2.7 times) compared to values for Voltarol® Retard with food of 0.093 to 0426 (4.6 times). In addition, diclofenac concentrations could be measured at later times for Formulation 7 (fed) than for Voltarole Retard (fed).

(2) The mean extend of bioavailability of Formulation 7 relative to Voltarole Retard when both formulations were administered following a high-fat meal, was 86% (SD 28%) and the 90% confidence interval for the difference did not include zero (−34% to −7%). However, it must be recognised that subjects whose profiles showed evidence of dose-dumping characteristics with the Voltarol® Retard formulation may have an over-estimation of their AUC values for the reference formulation.

(3) The range of maximum observed plasma concentrations for Formulation 7 was much less than for the reference formulation. For Formulation 7 (fed) the values ranged from 0.210 mg/L to 0.539 mg/L, while for Voltarole Retard the maximum observed plasma concentrations ranged from 0.157 mg/L to 1.659 mg/L. The difference in these ranges for the two formulations further indicates the greater in-vivo performance reproducibility for Formulation 7 compared with Voltarol® Retard.

(4) Food had no influence on the extend of bioavailability of diclofenac from Formulation 7. The 90% confidence interval for the difference ranged from −20% to +12%. Food, however, caused a significant increase in the time to reach maximum observed plasma concentration for Formulation 7 with the mean value increasing from 4.0 to 8.3 hours. This increase could, however, be explained by an increase in the lag time following administration of Formulation 7 with food. The maximum observed plasma concentration was slightly decreased, but the difference was not statistically significant which suggests that the rate of release from Formulation 7, once the lag time is reached, is not altered to any significant extent by the presence of food.

(5) The mean relative extent of absorption from Formulation 7 (fasting) was slightly higher (118%) than for Formulation 1 (fasting), although the difference was not statistically significant. The 90% confidence interval was −4.8% to +31.7%. The mean maximum observed plasma concentrations for both Formulations when given in the fasting state were not statistically different.

Conclusion

In conclusion, the data indicate that Formulation 7 provides better sustained-release characteristics than Voltarole Retard when both formulations are administered following food. The relative extent of bioavailability of Formulation 7 was slightly less than for Voltarol® Retard because of the method of determination of the AUC values used in the assessment of bioavailability which tended to underestimate this estimate of bioavailability.

TABLE 4

DICLOFENAC BIOAVAILABILITY STUDY NO. DIC-1/91
STATISTICAL COMPARISONS OF PHARMACOKINETIC PARAMETERS
AND OBSERVATIONS (n = 11)

Table 4A: FORMULATION 7 Capsules (fasting) vs FORMULATION 1 Capsules (fasting)

|  | Arithmetic Means ± SD | | Observed | 90% Confidence | |
| --- | --- | --- | --- | --- | --- |
|  | FORMULATION 7 | FORMULATION 1 | Difference | Interval (%) | |
|  | fasting | fasting | (%) | Lower Limit | Upper Limit |
| $AUC_{0-1}$ (mg.h/L) | 1.784 ± 0.521 | 1.573 ± 0.553 | +13.4 | −4.8 | +31.7 |
| F(%) (based on $AUC_{0-1}$) | 118.4 ± 26.3 | 100 | +18.4 | — | — |
| $C_{max}$ (mg/L) | 0.362 ± 0.118 | 0.336 ± 0.139 | +7.7 | −15.7 | +43.7 |
| $t_{max}$ (h) | 4.00 ± 0.77 | 3.64 ± 1.12 | +9.9 | Significance (p = 0.05)** $FORM^N$ 7 (fasting) = $FORM^N$ 1 (fasting) | |
| $t_{lag}$ (h) | 0.752 ± 0.340 | 0.682 ± 0.513 | +10.3 | — | — |

Table 4B: FORMULATION 7 Capsules (fed) vs FORMULATION 7 Capsules (fasting)

|  | Arithmetic Means ± SD | | Observed | 90% Confidence | |
| --- | --- | --- | --- | --- | --- |
|  | FORMULATION 7 | FORMULATION 1 | Difference | Interval (%) | |
|  | fed | fasting | (%) | Lower Limit | Upper Limit |
| $AUC_{0-1}$ (mg.h/L) | 1.710 ± 0.536 | 1.784 ± 0.521 | −4.1 | −20.2 | +11.9 |
| F(%) (based on $AUC_{0-1}$) | 98.6 ± 25.8 | 118.4 ± 26.3 | −1.4 | — | — |
| $C_{max}$ (mg/L) | 0.319 ± 0.105 | 0.362 ± 0.118 | −11.9 | −32.0 | +15.9 |
| $t_{max}$ (h) | 8.28 ± 2.28 | 4.00 ± 0.77 | +107.0 | Significance (p = 0.05)** $FORM^N$ 7(fed) > $FORM^N$ 7(fasting) | |
| $t_{lag}$(h) | 4.184 ± 1.660 | 0.752 ± 0.340 | +73.7 | — | — |

Table 4C: FORMULATION 1 Capsule (fed) vs REFERENCE, Voltarol Retard Tablet (fed)

|  | Arithmetic Means ± SD | | Observed | 90% Confidence | |
| --- | --- | --- | --- | --- | --- |
|  | FORMULATION 7 | REFERENCE* | Difference | Interval (%) | |
|  | fed | fed | (%) | Lower Limit | Upper Limit |
| $AUC_{0-1}$ (mg.h/L) | 1.710 ± 0.536 | 2.149 ± 0.862 | −20.4 | −33.8 | −7.1 |

TABLE 4-continued

DICLOFENAC BIOAVAILABILITY STUDY NO. DIC-1/91
STATISTICAL COMPARISONS OF PHARMACOKINETIC PARAMETERS
AND OBSERVATIONS (n = 11)

| | | | | | |
|---|---|---|---|---|---|
| F(%) (based on $AUC_{0-1}$) | 98.6 ± 25.8 | 100 | −13.7 | — | — |
| $C_{max}$ (mg/L) | 0.319 ± 0.105 | 0.734 ± 0.429 | −56.5 | −61.5 | −34.3 |
| $t_{max}$ (h) | 8.28 ± 2.28 | 4.73 ± 2.28 | +75.1 | Significance (p = 0.05)** $FORM^N$ 7(fed) > REFERENCE (fed) | |
| $t_{lag}(h)$ | 4.184 ± 1.660 | 2.409 ± 1.773 | +73.7 | — | — |

*Values normalised (× 318/296) relative to diclofenac acid
**Determined using nonparametric Freidman test

TABLE 5

Mean (SD) Plasma Diclofenac Concentrations (mg/L) at Nominated Sampling Times (h)

| | Mean Plasma Concentration (mg/L) | | | | Form. 7 fasting vs/ Form 1 fasting 90% Confidence Interval (%) | | Form 7 fed vs. Form 7 fasting 90% Confidence Interval (%) | | Form. 7 fed vs. Reference fed 90% Confidence Interval (%) | |
|---|---|---|---|---|---|---|---|---|---|---|
| | (a) | (b) | (c) | (d)* | Lower Limit | Upper Limit | Lower Limit | Upper Limit | Lower Limit | Upper Limit |
| Nominal Time (h) | Form. 1 fasting | Form. 7 fed | Form. 7 fasting | Reference fed | | | | | | |
| 0.00 | 0.000 (0.000) | 0.000 (0.000) | 0.000 (0.000) | 0.000 (0.000) | — | — | — | — | — | — |
| 0.25 | 0.000 (0.000) | 0.000 (0.000) | 0.000 (0.000) | 0.000 (0.000) | — | — | — | — | — | — |
| 0.50 | 0.013 (0.025) | 0.000 (0.000) | 0.002 (0.008) | 0.003 (0.009) | −161.6 | −7.6 | 600.5 | 400.5 | −433.7 | 233.7 |
| 0.75 | 0.042 (0.043) | 0.000 (0.000) | 0.026 (0.042) | 0.006 (0.013) | −92.8 | 16.6 | −188.3 | −11.7 | −482.7 | 282.7 |
| 1.00 | 0.066 (0.081) | 0.000 (0.000) | 0.049 (0.043) | 0.009 (0.016) | −75.0 | 23.5 | −166.3 | −33.7 | −460.6 | 260.8 |
| 1.50 | 0.125 (0.137) | 0.000 (0.000) | 0.092 (0.076) | 0.000 (0.000) | −71.4 | 18.6 | −165.1 | −38.9 | — | — |
| 2.00 | 0.153 (0.142) | 0.000 (0.000) | 0.144 (0.104) | 0.128 (0.264) | −85.3 | 73.5 | −184.4 | −15.6 | −194.9 | −5.1 |
| 3.00 | 0.251 (0.165) | 0.004 (0.014) | 0.243 (0.122) | 0.251 (0.351) | −60.3 | 54.0 | −157.4 | −39.3 | −155.5 | −41.3 |
| 4.00 | 0.253 (0.109) | 0.037 (0.079) | 0.312 (0.147) | 0.432 (0.521) | −51.5 | 98.2 | −148.8 | −27.5 | −135.3 | −47.6 |
| 5.00 | 0.208 (0.071) | 0.114 (0.107) | 0.228 (0.042) | 0.252 (0.176) | −31.7 | 50.9 | −87.7 | −12.3 | −88.9 | −20.7 |
| 6.00 | 0.130 (0.073) | 0.163 (0.120) | 0.150 (0.043) | 0.143 (0.101) | −31.4 | 62.1 | −31.8 | 49.2 | −28.5 | −56.5 |
| 8.00 | 0.080 (0.057) | 0.172 (0.092) | 0.090 (0.037) | 0.235 (0.305) | −136.7 | 161.7 | −41.5 | 223.7 | −77.6 | 24.0 |
| 10.00 | 0.053 (0.031) | 0.212 (0.170) | 0.058 (0.025) | 0.154 (0.222) | −169.2 | 188.1 | 102.3 | 428.8 | −23.8 | 99.1 |
| 12.00 | 0.033 (0.022) | 0.151 (0.102) | 0.048 (0.023) | 0.045 (0.065) | −75.1 | 166.0 | 131.7 | 297.4 | 147.2 | 323.9 |
| 14.00 | 0.019 (0.024) | 0.054 (0.032) | 0.031 (0.027) | 0.017 (0.033) | −57.7 | 184.0 | 0.1 | 148.3 | 82.6 | 352.7 |
| 16.00 | 0.012 (0.018) | 0.026 (0.024) | 0.022 (0.023) | 0.009 (0.020) | −2.3 | 168.9 | −28.5 | 64.9 | 74.8 | 303.0 |
| 20.00 | 0.000 (0.000) | 0.006 (0.014) | 0.003 (0.011) | 0.000 (0.000) | — | — | −102.5 | 302.5 | — | — |
| 24.00 | 0.026 (0.022) | 0.028 (0.032) | 0.040 (0.033) | 0.004 (0.014) | −2.0 | 109.7 | −66.3 | 6.3 | 236.9 | 963.1 |

*Values normalised (*318/296) relative to diclofenac acid

Finally, it is to be understood that various other modifications and/or alterations may be made without departing from the spirit of the present invention as outlined herein.

5. Part E. Analgesic Efficacy of sustained Release Diclofenac (Formulation 7)

A study to determine the Analgesic Efficacy of the Sustained Release Diclofenac Acid Formulation (SRDA) according to the invention (formulation 7) following single and multiple doses in patients with Musculoskeletal Disease was undertaken.

The objectives were:

1. To evaluate the time course of analgesic effect following a single oral dose of the SRDA formulation.
2. To evaluate the time course of analgesic effect following multiple oral doses of SRDA 150 mg.
3. To evaluate whether tolerance to the analgesic effect occurs following multiple dosing with SRDA.

This was determined by comparing the analgesic effects following:

(i) a single dose of SRDA 150 mg.
(ii) multiple doses of SRDA 150mg, one capsule daily for five to six doses.
(iii) a single dose of SRDA 150 mg following multiple doses of placebo.

DESIGN

In a randomised, double blind study, seventy five patients aged 22 to 74 (median, 44 years) with stable pain due to musculoskeletal disorders of moderate to sever intensity and who had not undergone surgery or physical manipulation in the three months prior to entry, were screened for the study. Sixty patients received treatment with SRDA. Fifty five patients completed the study, one patient's data were not evaluable. Five patients withdrew from the study.

TREATMENT

Patients were randomised to one of four parallel groups.

During the eight day treatment period patients received diclofenac (SRDA) 150 mg or matching placebo capsule at approximately 21 00h each evening according to the randomisation schedule. The relationship of dosing to meals was not recorded.

PRIMARY OUTCOME

The primary measures of efficacy were pain intensity and pain relief scores which were evaluated on days 1, 2, 3, 7, 8 and 9 using 100 mm visual analogue scales (VAS).

In addition, the time(s) and dose(s) of rescue analgesia throughout the NSAID washout period and treatment periods were recorded.

MEASUREMENTS

Pain intensity and pain relief scores were measured using 100 mm visual analogue scales (VAS) on the following days:
On days 1, 2, 7 and 8:
Pain intensity scores immediately before the dose; and
Pain intensity and pain relief scores at one hour after dose administration (at approximately 22 00h).
On days 2, 3, 8 and 9:
Pain intensity and pain relief scores on waking and every two hours throughout the day.

RESULTS

Efficacy

Following a single oral dose of SRDA 150 mg given once daily at 21 00h there was little change in pain intensity over the first one to two hours. However, there was a clinically and statistically significant reduction in pain intensity from waking the next morning until the time of the next SRDA dose.

The analgesic effect of a single oral dose of SRDA 150 mg was still apparent during the day following a placebo capsule given 24 hours after the initial dose of SRDA 150 mg. Residual carry-over effects or analgesic effects may be present for up to five or six days following a single oral dose of SRDA 150 MG.

The time course of analgesic effect during multiple dosing with SRDA 150mg given once daily at 21 00h for five or six doses was similar to that following single oral doses.

There was no tolerance in analgesic effect with SRDA 150 mg given daily at 21 00h for five of six consecutive doses.

Overall, single oral doses of SRDA 150 mg resulted in a clinically significant, moderate reduction in pain intensity of about 37% compared to baseline.

There was no statistically significant difference in rescue analgesia use in the SRDA treatment periods compared to placebo treatment periods.

VAS of pain relief were less reliable measures of analgesic effect than VAS of pain intensity.

Safety

The most frequently reported adverse events were: headache (47%), nausea (11%), constipation, abdominal upsets and flu or flu-like symptoms. The number of adverse events reported by patients in the diclofenac treatment groups was statistically significantly greater than the number of adverse events reported by patients in the placebo treatment groups.

Of the 128 adverse events reported by forty one of the sixty patients, 11 % were reported as severe. None of the adverse events were serious adverse events.

CONCLUSIONS

Single oral doses of SRDA 150 mg result in an overall reduction in pain intensity of 37% in patients with stable, chronic pain of musculoskeletal disorders. There was a lag of one to two hours in the effect on pain intensity but the effect is maintained for at least 24 hours.

Multiple doses of SRDA 150 mg daily for five or six consecutive doses result in a similar time course of analgesic effect with no evidence of tolerance.

There were significantly more adverse events reported during the SRDA 150 mg treatment groups. The most common adverse events were headache, nausea, constipation, abdominal upsets and flu or flu-like symptoms. They were generally mild and single or intermittent.

We claim:

1. A pelletized sustained release pharmaceutical composition comprising
   a core element comprising
   approximately 0.1 to 95% weight, based on the total weight of the core element of an active ingredient of low aqueous solubility,
   approximately 0.1 to 55% by weight weight binding agent;
   approximately 5 to 99% weight of a core seed; and
   a core coating for the core element, comprising
   approximately 30 to 97% by weight, based on the total weight of the core coating, excluding filler, of an enteric polymer;
   approximately 3 to 50% by weight of an insoluble polymer; and
   0 to approximately 50% by weight of plasticizer, the enteric polymer comprising at least approximately 70% by weight of the total weight of the enteric polymer and insoluble polymer;
   the core coating being such that the active ingredient is released in a controlled fashion over an extended period in the intestine but substantially no release occurs in the acid environment of the stomach and blood levels of active ingredient are maintained within the therapeutic range over an extended period of time.

2. The pelletized pharmaceutical composition of claim 1 wherein the active ingredient is erythromycin.

3. The pelletised pharmaceutical composition of claim 1 wherein the active ingredient is a non-steroidal anti-inflammatory drug (NSAID) or an acid or salt thereof.

4. The pelletised pharmaceutical composition of claim 3 wherein the active ingredient is selected from a low aqueous solubility form of Diclofenac, Ketorolac and Indomethacin.

5. The pharmaceutical composition of claim 4 wherein the active ingredient comprises Diclofenac.

6. The pharmaceutical composition of claim 1 wherein the core coating further comprises
   up to 75% by weight of a filler; and
   up to 60% by weight of a water soluble component.

7. The pelletised pharmaceutical composition of claim 1, wherein the core element includes approximately 0.1 to 45% by weight of a binding agent selected from the group consisting of polyvinylpyrrolidone (povidone), hydroxypropyl cellulose, hydroxypropyl methylcellulose, methylcellulose, hydroxyethyl cellulose, sugars and mixtures thereof.

8. The pelletised pharmaceutical composition of claim 7 wherein the core coating comprises
   approximately 70 to 87% by weight of an enteric polymer selected from the group consisting of cellulose butyrate phthalate, cellulose hydrogen phthalate, cellulose propionate phthalate, polyvinyl acetate phthalate, cellulose acetate phthalate, cellulose acetate trimellitate, hydroxypropyl methylcellulose phthalate, hydroxypropyl methylcellulose acetates, dioxypropyl methyl cellulose succinates, acrylic methacrylic acid copolymers, shellac, copal collophorium, cellulose acetate phthalate and mixtures thereof; and
   approximately 3 to 50% by weight of an insoluble polymer component selected from the group consisting of ethyl cellulose, cellulose acetates and their esters, acrylic methacrylic acid copolymers, hydroxypropyl methyl cellulose acetate and mixtures thereof.

9. The pelletised pharmaceutical composition of claim 8 wherein the core coating comprises approximately 2.5 to 30% by weight of a plasticiser selected from diethyl phthalate, triethyl citrate, triethyl acetyl citrate, triacetin, tributyl citrate, polyethylene glycol, glycerol and mixtures thereof.

10. A method for preparing a pelletized sustained release pharmaceutical composition, which method comprises providing a core element comprising approximately 0.1 to 95% weight, based on the total weight of the core element of an active ingredient of low aqueous solubility, approximately 0.1 to 55% by weight of a binding agent;

approximately 5 to 99% weight of a core seed; and a core coating for the core element, including approximately 30 to 97% by weight, based on the total weight of the core coating, excluding filler, of an enteric polymer;

approximately 3 to 50% by weight of an insoluble polymer, the enteric polymer comprising at least approximately 70% by weight of the total weight of the enteric polymer and insoluble polymer; and spraying the core coating composition onto the core element.

11. The method of claim 10, further comprising the preliminary steps of providing
an active ingredient of low aqueous solubility;
a binding agent; and
a core seed; and coating the core seed with the active ingredient and binding agent to form a core element.

12. The method according to claim 10 further comprising the preliminary steps of providing
at least one active ingredient of low aqueous solubility;
an effective amount of a solvent or granulating liquid, mixing the ingredients; and subjecting the ingredients to an extrusion followed by marumerisation to form a core element.

13. A method for the therapeutic or prophylactic treatment of conditions in patients requiring treatment, which method includes administering to a patient an effective amount of a pelletized sustained release pharmaceutical composition comprising a core element comprising approximately 0.1 to 95% weight, based on the total weight of the core element of an active ingredient of low aqueous solubility selected from diclofenac, ketorolac and indomethacin, approximately 0.1 to 55% by weight weight binding agent;

approximately 5 to 99% weight of a core seed; and a core coating for the core element, including approximately 30 to 97% by weight, based on the total weight of the core coating, excluding filler, of an enteric polymer;

approximately 3 to 50% by weight of an insoluble matrix polymer; and 0 to approximately 50% by weight of plasticizer, the enteric polymer comprising at least approximately 70% by weight of the total weight of the enteric polymer and insoluble matrix polymer;

the core coating being such that the active ingredient is released in a controlled fashion over an extended period in the intestine but substantially no release occurs in the acid environment of the stomach and blood levels of active ingredient are maintained within the therapeutic range over an extended period of time.

14. A sustained release pharmaceutical composition comprising pellets from about 0.5 mm to about 2 mm in size which include:

a core element comprising, based on the total weight of the core element:
about 0.1 to 95% weight of an active ingredient of low aqueous solubility;
about 0.1 to 55% by weight of a binding agent;
about 5 to 99% weight of a core seed; and a core coating for the core element, based on the total weight of the core coating, excluding filler, comprising:
about 3 to 50% by weight of an insoluble polymer
about 30 to 97% by weight of an enteric polymer, the enteric polymer comprising at least about 70% by weight of the total weight of the enteric polymer and insoluble polymer; and
up to about 50% by weight of plasticizer;

wherein the core coating is such that the active ingredient is released in a controlled fashion in the intestine so that the blood level of the active ingredient is maintained within a therapeutically effective range over an extended period and is not substantially released in the stomach.

* * * * *